US009820734B2

(12) United States Patent
Gittard

(10) Patent No.: US 9,820,734 B2
(45) Date of Patent: Nov. 21, 2017

(54) DEVICE FOR CUTTING SUTURE FROM A DISTANCE

(71) Applicant: Cook Medical Technologies LLC, Bloomington, IN (US)

(72) Inventor: Shaun Davis Gittard, Winston Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 205 days.

(21) Appl. No.: 14/748,520

(22) Filed: Jun. 24, 2015

(65) Prior Publication Data
US 2015/0366557 A1    Dec. 24, 2015

Related U.S. Application Data

(60) Provisional application No. 62/016,423, filed on Jun. 24, 2014.

(51) Int. Cl.
*A61B 17/10* (2006.01)
*A61B 17/04* (2006.01)
*A61B 17/00* (2006.01)

(52) U.S. Cl.
CPC ..... *A61B 17/0467* (2013.01); *A61B 2017/00398* (2013.01); *A61B 2017/00544* (2013.01)

(58) Field of Classification Search
CPC . A61B 17/04; A61B 17/0467; A61B 17/0469; A61B 17/0482; A61B 2017/00398; A61B 2017/00544; A61B 17/10
See application file for complete search history.

(56) References Cited

U.S. PATENT DOCUMENTS

| 1,324,976 | A |   | 12/1919 | Oesterwitz |
|-----------|---|---|---------|------------|
| 1,448,858 | A |   | 3/1923  | Oesterwitz |
| 3,328,876 | A |   | 7/1967  | Hoppe |
| 3,802,074 | A |   | 4/1974  | Hoppe |
| 5,405,351 | A |   | 4/1995  | Kinet et al. |
| 5,549,623 | A |   | 8/1996  | Sharpe et al. |
| 6,004,332 | A | * | 12/1999 | Yoon ............... A61B 17/0469 606/139 |
| 7,833,237 | B2 |  | 11/2010 | Sauer |
| 8,469,983 | B2 |  | 6/2013  | Fung et al. |

(Continued)

OTHER PUBLICATIONS

Cardinal Search Report dated Jan. 28, 2014.

*Primary Examiner* — Victor Nguyen
(74) *Attorney, Agent, or Firm* — Brinks Gilson & Lione

(57) ABSTRACT

The present disclosure provides a cutting assembly for cutting an object, such as a suture, within the body of a patient. The cutting assembly includes a housing, a proximal cutting element, a distal cutting element, and an actuating member. Both the proximal and distal cutting elements have a cutting surface or blade. The blades face each other within the housing and actuate towards each other to cut the suture. The housing further includes a plurality of slots that house the blades and maintain them in the orientation desired for cutting. The housing further includes openings to guide the suture through the cutting assembly. The cutting assembly provides sufficient flexibility to be oriented at the suture location, but maintains its rigidity to effectuate a sufficient, clean cut.

19 Claims, 9 Drawing Sheets

(56) References Cited

U.S. PATENT DOCUMENTS

| | | |
|---|---|---|
| 2006/0241665 A1 | 10/2006 | Bosley et al. |
| 2007/0027457 A1 | 2/2007 | Walborn |
| 2008/0228198 A1 | 9/2008 | Traynor et al. |
| 2009/0259234 A1 | 10/2009 | Waller |
| 2010/0069922 A1 | 3/2010 | Kaufman |
| 2013/0274722 A1 | 10/2013 | Kostrzewski et al. |

* cited by examiner

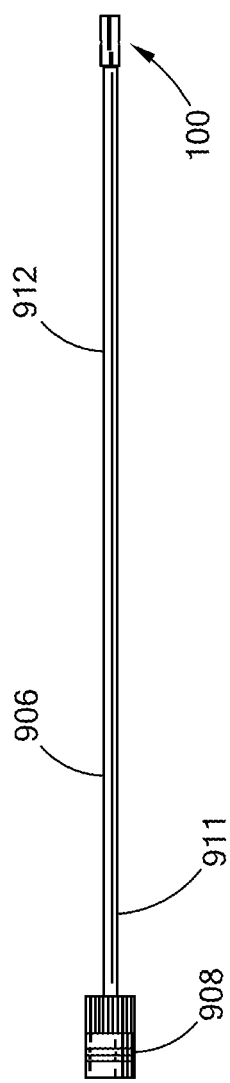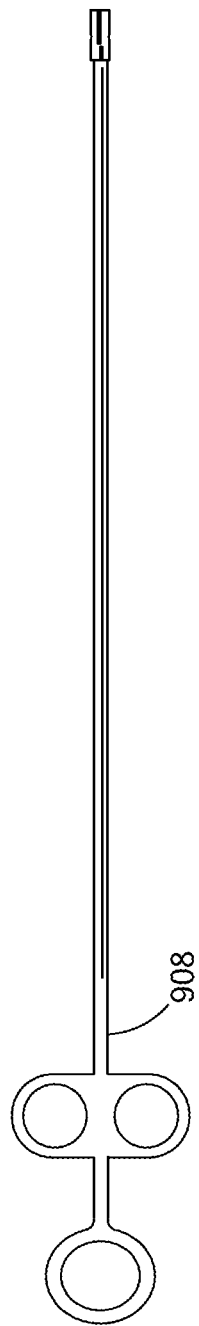
Fig. 9A
Fig. 9B

DEVICE FOR CUTTING SUTURE FROM A DISTANCE

CROSS-REFERENCE TO RELATED APPLICATIONS

This application claims priority to U.S. Provisional Patent Application Ser. No. 62/016,423, filed Jun. 24, 2014, entitled "DEVICE FOR CUTTING SUTURE FROM A DISTANCE," the entire contents of which are hereby incorporated by reference.

BACKGROUND

1. Technical Field

The present disclosure relates to medical devices. More particularly, the disclosure relates to a device or cutting assembly for cutting a suture in the body of a patient.

2. Background Information

Surgical sutures are one of the most commonly used medical devices, often used to stitch up an incision site or hold body tissues together. In the advent of minimally invasive surgical procedures, such incision sites can occur deep within the patient's body without easy access to the practitioner. To perform suturing, the practitioner ties a stitch or a knot outside of the body and pushes it down to the suture or incision site. However, the practitioner often has difficulty seeing where to cut the excess piece of suture material after the last knot is tied at the incision site. X-ray technology and cameras aids in visualization of equipment, but may do little to assist in visualization of the suture itself for making these remote cuts.

Additionally, even if the practitioner achieves sufficient visualization using a camera, he or she still may have difficulty preforming the remote cut with current cutting devices. Current cutting devices often must have sufficient flexibility to reach a remote suture site within the patient's body, but this flexibility reduces the strength necessary to make a sufficient, clean cut of the excess suture material. Further, some current cutting devices result in merely pushing the suture material, but failing to make a cut. There exists a need for a cutting device that solves the problems of sufficient remote visualization and cutting.

BRIEF SUMMARY

The present disclosure provides a cutting assembly for cutting a suture or object in a remote location of the body of a patient. The cutting assembly may include a housing being tubular and having a proximal end and extending along a longitudinal axis to a distal end with a housing lumen formed therethrough. The cutting assembly may further include a proximal cutting element disposed in the housing lumen and having a first end distal the proximal end. The first end may extend along the longitudinal axis to a second end, defining a first plane. The second end may have a proximal cutting surface.

The cutting assembly may further include a distal cutting element disposed in the housing lumen distal the proximal cutting element and include a third end extending along the longitudinal axis to a fourth end, defining a second plane being parallel with the first plane. The third end may include a distal cutting surface. One of the proximal and distal cutting elements may be operable along the longitudinal axis such that the cutting assembly has an open position and a closed position. The distal cutting surface may be distal the proximal cutting surface a first distance (d) in the open position. In addition, the distal cutting surface may be proximal the proximal cutting surface a second distance (o) in the closed position. The proximal and distal cutting surfaces may cooperate to cut the object in the body. In one embodiment, both cutting elements actuate or move. Alternatively, only one of the cutting elements moves.

In one embodiment, the proximal and distal cutting surfaces are linear. In another embodiment, the proximal and distal cutting surfaces are V-shaped or concave to push the object to the center of the cutting surfaces for cutting. The housing can be made of any material suitable for cutting. In particular, the material may be uniform or it may vary along the dimensions of the housing, being a plurality of materials.

The housing has an inner wall forming a plurality of slots. The plurality of slots may be a first slot and a second slot. The second slot may be parallel with the first slot. The first slot may be formed across the housing lumen from the second slot, the first and second slots being parallel with the longitudinal axis.

The plurality of slots may include a third slot and a fourth slot. The third slot may be proximal the first slot. The fourth slot may be proximal the second slot. The third slot may be parallel with and formed across the housing lumen from the fourth slot, the third and fourth slots being parallel with the longitudinal axis.

The proximal cutting element comprises a proximal shoulder disposed on its first end, disposed in the third and fourth slots. Similarly, the distal cutting element comprises a distal shoulder disposed on its fourth end, the distal shoulder disposed in the first and second slots. At least one slot has a stop element, the stop element disposed to fill a portion of the at least one slot to stop one of the proximal and distal shoulders from sliding beyond a given point or position.

The housing may have a first opening disposed between the proximal and distal ends and a second opening being formed across the housing lumen from the first opening such that the object is disposed in the first and second openings and between the proximal and distal cutting surfaces. The assembly may further have a hollow tube disposed and slidably received in the first and second openings to accommodate the object to be cut. Optionally, the housing has an elongate member disposed around it. The elongate member also runs along the longitudinal axis. In one embodiment, during actuation the distal cutting element moves or slides adjacent the proximal cutting element when moving from the open position to the closed position.

The proximal and distal cutting elements are disposed parallel to each other and in different planes so that the distal cutting element moves adjacent to the proximal cutting element. In the open position, the proximal and distal cutting elements are disposed apart the first distance (d) being sized and shaped to accommodate the object. In the closed position, the proximal and distal cutting elements may be separated by the second distance (o).

The cutting assembly further comprises a handle being proximal the proximal end. The handle may be connected to an actuating member such that the actuating member distally extends along the longitudinal axis to the one of the proximal and distal cutting elements. In other words, the actuating member operates the one of the proximal and distal cutting elements. In one embodiment, the actuating member is a metal stylet.

In one embodiment, the actuating member comprises a first actuator, or first actuating member, and a return member. The first actuator actuates the distal cutting element toward the proximal cutting element moving the cutting assembly from the open position to the closed position. In other words, the first actuating member may be mechanically connected to and slidably operating the distal cutting element, the proximal cutting element being stationary. The return member (e.g. a spring) actuates or moves the distal cutting element away from the proximal cutting element moving the cutting assembly from the closed position to the open position. The spring may biasingly move the cutting assembly from the closed position to the open position.

The actuating member may further have a second actuator. The first actuator actuates the distal cutting element and the second actuator, or second actuating member, operates or actuates the proximal cutting element between the open and closed positions.

This disclosure also provides a method of cutting an object. The method may include (1) positioning the object within a cutting assembly, as described herein; (2) introducing the cutting assembly in the body; and (3) operating the one of the proximal and distal cutting elements to cut the object.

In one embodiment, the object to be cut is a suture. Optionally, the suture may be disposed within the hollow tube. The first distance (d) may be size and shaped to accommodate the hollow tube. The tube may be slidably removed before cutting.

BRIEF DESCRIPTION OF THE DRAWINGS

FIGS. 9A-B depict side views of the cutting assembly of FIG. 1.

DETAILED DESCRIPTION OF THE DRAWINGS

The present disclosure provides a cutting assembly for cutting a suture or object in the body of a patient. The disclosure details embodiments of a cutting assembly and methods of cutting. The cited figures illustrate these different embodiments and methods.

The accompanying figures are provided for general understanding of the structure of various embodiments. However, this disclosure may be embodied in many different forms. These figures should not be construed as limiting and they are not necessarily to scale.

Figure 1:
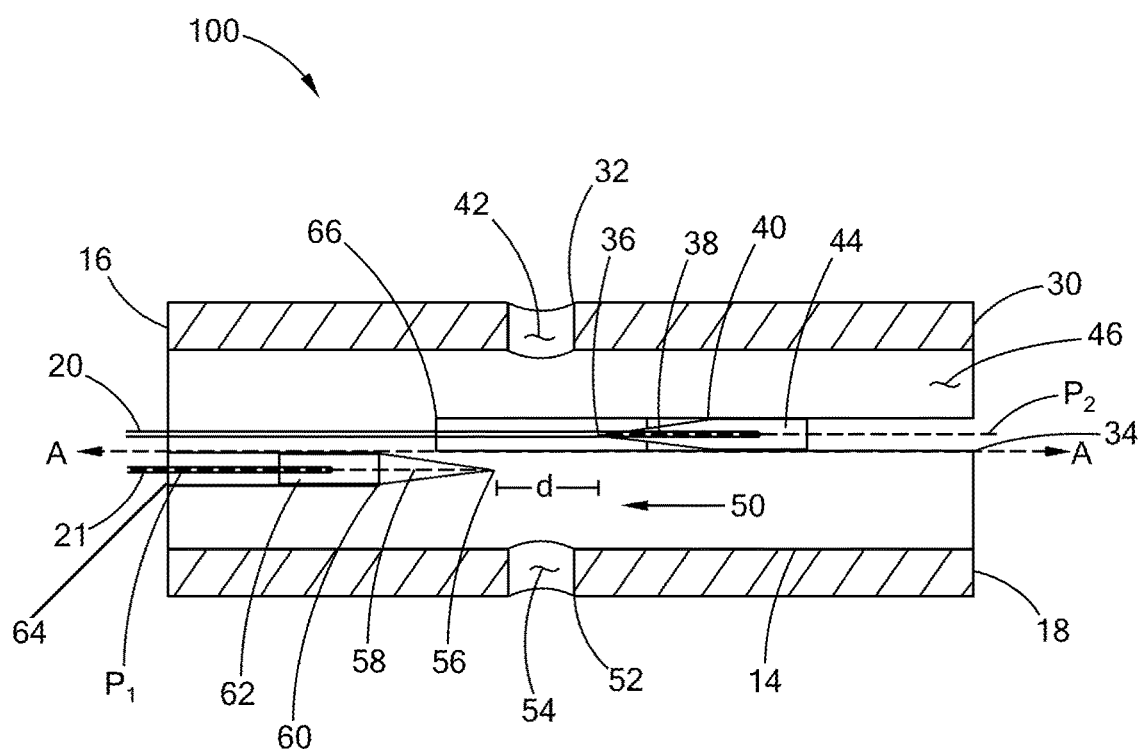
FIG. 1 depicts a partial, side view of a cutting assembly in accordance with one embodiment of the present invention.

The cutting assembly moves from an open position to a closed position to cut the object. FIG. 1 shows one embodiment of an open position of a cutting assembly. In this embodiment, the cutting assembly 100 has a housing 30, a pair of cutting elements (58, 38), and a pair of actuating members (20, 21). Housing 30 is located outside of and may form the outer barrier of the cutting assembly 100. In one embodiment, housing 30 is a cannula. Housing 30 has a housing lumen 46 that runs along the longitudinal axis A of the cutting assembly. The housing may be tubular to fit within the vasculature. The housing 30 has a proximal end 16 extending along the longitudinal axis A to a distal end 18. The housing 30 further includes an inner wall 14.

Housing 30 can be formed from any material suitable to house the cutting elements. It can be a ridged, semi-ridged, or flexible material. The material may be uniform along the housing's dimensions. Alternatively, the material can vary along the length, width, or circumference of the housing. The housing may be a rigid material, such as metal, to keep the cutting elements or blades in an optimal cutting position, preventing movement along multiple axes. The cutting elements may move only along one axis.

Proximal cutting element 58 and distal cutting element 38 are disposed within housing 30. Two cutting elements provide increased tension on the object during cutting to make a sufficient, clean cut, similar to the action of a scissors. The distal cutting element 38 has a third end 36 and a fourth end 40, defining or forming a second plane $P_2$. The third end 36 is the distal cutting surface.

Proximal cutting element 58 has a first end 60 and a second end 56, defining a first plane $P_1$. The second end 56 is the proximal cutting surface. In the open position, distal cutting element 38 is separated from proximal cutting element 58 by a first distance (d). This first distance (d) is sized and shaped to accommodate the object to be cut. For example, if the object is a suture, first distance (d) must be large enough to accommodate the size of the suture. In another embodiment, the object may be shielded or housed in a hollow tube, such as a catheter (not shown). In this embodiment, first distance (d) must be large enough to accommodate the tube. After positioning the tube, the practitioner removes it and exposes the suture before cutting.

The cutting elements are operable along the longitudinal axis such that the cutting assembly moves between the open position and the closed position. The distal cutting element 38 may move in a direction of arrow 50 towards and adjacent to the proximal cutting element 58 to cut the object. "Adjacent" means that the distal cutting element is located next to or near the proximal cutting element, such that it slides next to or near the proximal cutting element, as shown in FIG. 1. This movement results from one or more actuating members (20, 21). Here, the proximal and distal cutting surfaces cooperate to cut the object.

In one embodiment, the cutting assembly includes an actuating member operating one of the proximal and distal cutting elements. For example, the first actuating member 20 is mechanically connected to and slidably operates the distal cutting element, and pulls the distal cutting element towards the proximal cutting element. The first actuating member 20 also may act to move the distal cutting element back, away from the proximal cutting element. This moves the assembly from the open to the closed position, and back to the open position. In this embodiment, the proximal cutting element is fixed or immobilized. The proximal cutting element may be immobilized by any method known in the art such as gluing, soldering, welding, or chemically bonding to the housing 30.

In a preferred embodiment, the first actuating member 20 is a metal stylet connected to the distal cutting element and extending proximally along the housing to a handle, outside of patient's body. In this embodiment, the metal stylet is connected to a handle that the practitioner operates to actuate the distal cutting element. Alternatively, the actuating member may be a thread or suture to move the assembly from the open position to the closed position. It will be understood that the first actuating member 20 may also be connected to another part or portion of the distal cutting element or the cutting assembly.

The actuating member may include a return member to actuate or return the cutting assembly from the closed position to the open position. The return member may be a spring or other means known in the art to return the cutting assembly from the closed to the open position by biasingly moving the cutting assmebly.

A skilled artisan will understand that the actuating member may be any type of actuating member to move the distal cutting element without falling beyond the spirit or scope of this disclosure. Instead of pulling the distal cutting element, the actuating member may alternatively push the distal cutting element to achieve actuation. In addition, the actuating member may be electrically or pneumatically driven. Further, in a preferred embodiment, the actuating member may actuate both the proximal and distal cutting elements. The actuating member may be a mechanical means connected to and moving both proximal and distal cutting elements. The cutting assembly can comprise a first actuating member 20 and a second actuating member 21. The first actuating member 20 may be connected to the distal cutting element and the second actuating member 21 may be connected to the proximal cutting element by any method known in the art such as gluing, soldering, welding, or chemical bonding. The second actuating member 21 may slidably operate the proximal cutting element to slide between the open and closed positions.

Figure 5A:
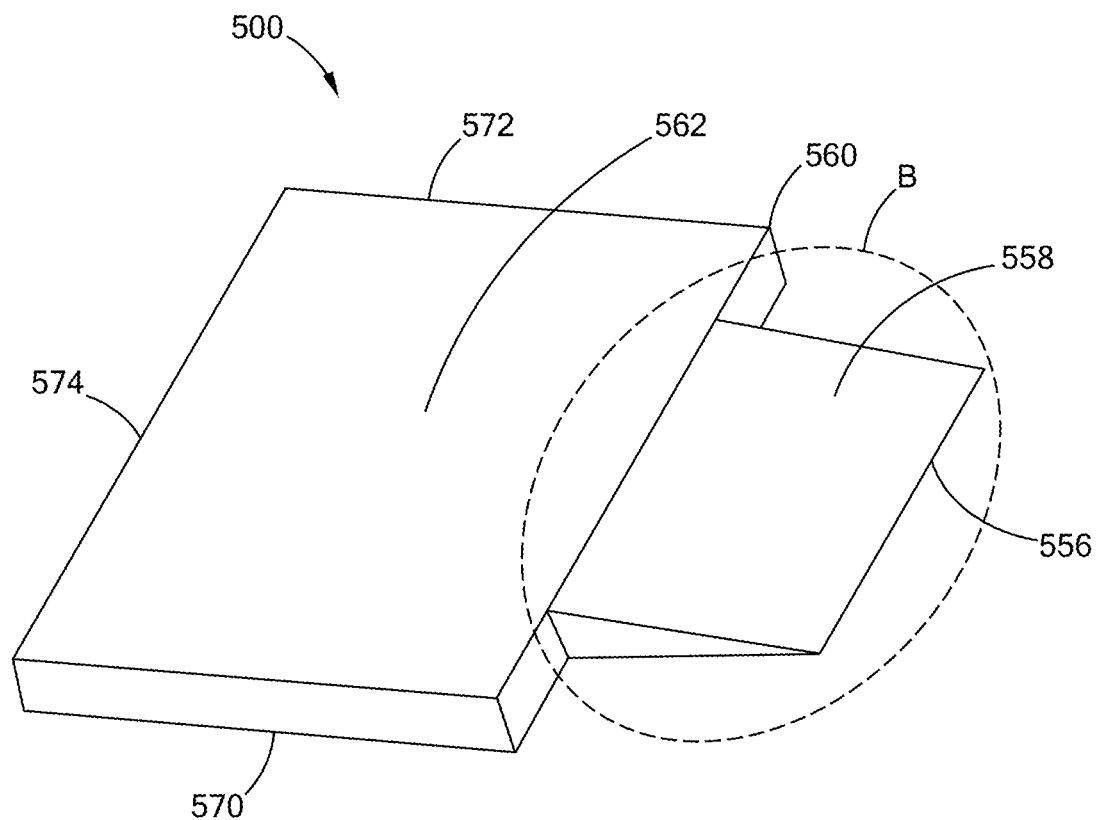
FIGS. 5A-B depict partial views of a proximal cutting element of the cutting assembly of FIG. 1.

In one embodiment, the proximal and distal cutting surfaces are a straight surface (shown in FIG. 5A). In an alternative embodiment, the proximal and distal cutting surfaces may have an alternative shape. For example, they could be concave or V-shaped to better orient and position the object for cutting (shown in FIG. 5B). Such an alternative shape aids to orient the object if there is a tube surrounding and protecting the suture. This alternative shape slides the tube into the middle of the cutting elements for easier cutting.

Figure 2:
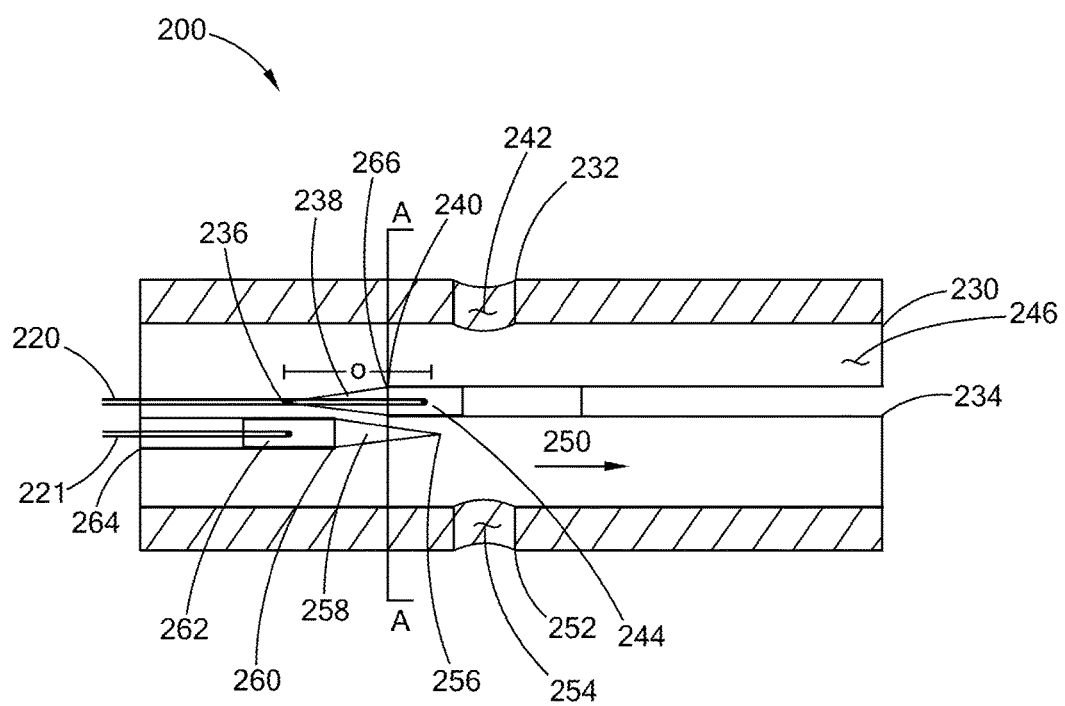
FIG. 2 depicts a partial, side view of the cutting assembly of FIG. 1.

FIG. 2 shows one embodiment of a closed position of the cutting assembly 200. Housing 230 comprises longitudinally running housing lumen 246. Distal cutting element 238 (having third and fourth ends (236, 240)) is actuated into the closed position by the first actuating member 220. In the closed position, it overlaps with the proximal cutting element 258 by an overlap or second distance (o). Proximal cutting element 258 comprises first end 260 and second end 256. To reopen the cutting assembly, the practitioner actuates the cutting assembly along arrow 250.

Returning to FIG. 1, the cutting assembly has an inner wall 14 forming a plurality of slots that aid in positioning of the cutting elements. A first slot 34 is formed in housing 30 and located parallel to and across the housing lumen 46 from a second slot (further shown in FIG. 3). The cutting assembly further comprises a third slot 64 formed in housing 30 and located parallel to and across the housing lumen 46 from a fourth slot (also shown in FIG. 3). The slots are disposed longitudinally along housing lumen 46.

Distal cutting element 38 and proximal cutting element 58 further comprise distal shoulder 44 and proximal shoulder 62, respectively. Shoulders 44 and 62 fit and slide inside slot 34 and slot 64, respectively. Positioning the shoulders of the cutting elements inside the slots helps maintain positioning of the cutting elements as they move inside the cutting assembly. The shoulder and slot fittings restrict the cutting elements so they only actuate or move along one axis, and do not rotate or shift out of position.

In the open position, distal cutting element 38 is disposed within the first slot 34, and is positioned away from either end of the slot so that it may slide or travel along the length of the slot to make the cut. Optionally, the cutting assembly comprises a stop element to prevent the cutting elements (e.g. at respective shoulders) from actuating or moving further along a slot. For example, in slot 34 there is stop element 66 located at the end of slot 34. A skilled artisan will understand that the stop element could alternatively be on an actuating member such that the practitioner would be prevented from pulling or pushing the actuating member beyond a certain distance. Additionally, the positive step could be a solid or slotted cylinder placed inside or in series with housing 30 to stop the cutting element from further moving along the direction of arrow 50.

The cutting assembly further comprises a guiding system for the object. In FIG. 1, the guiding system is a plurality of openings. First opening 32 is located on one end of the housing 30 and second opening 52 is located opposite and across the housing lumen from the first opening 32, on the other end of the housing 30. First opening lumen 42 is formed through first opening 32 and second opening lumen 54 is formed through second opening 52. These openings allow an object to align in both the first and second openings (32, 52) so that the object runs between and perpendicular to the cutting elements for optimal cutting. Openings 32 and 52 may be centered between the proximal and distal cutting elements in the open position.

In FIG. 2, slots 264 and 234 respectively contain or house proximal and distal shoulders (262, 244). Slots 234 also has stop element 266. Openings 232 and 252 guide the suture into placement for cutting. First opening 232 comprises first opening lumen 242, and second opening 252 comprises second opening lumen 254. The first and second opening lumens run perpendicular to the cutting elements and the longitudinal axis. Cross section A shows a cross section of the cutting assembly, further illustrated in FIG. 3.

Figure 3:
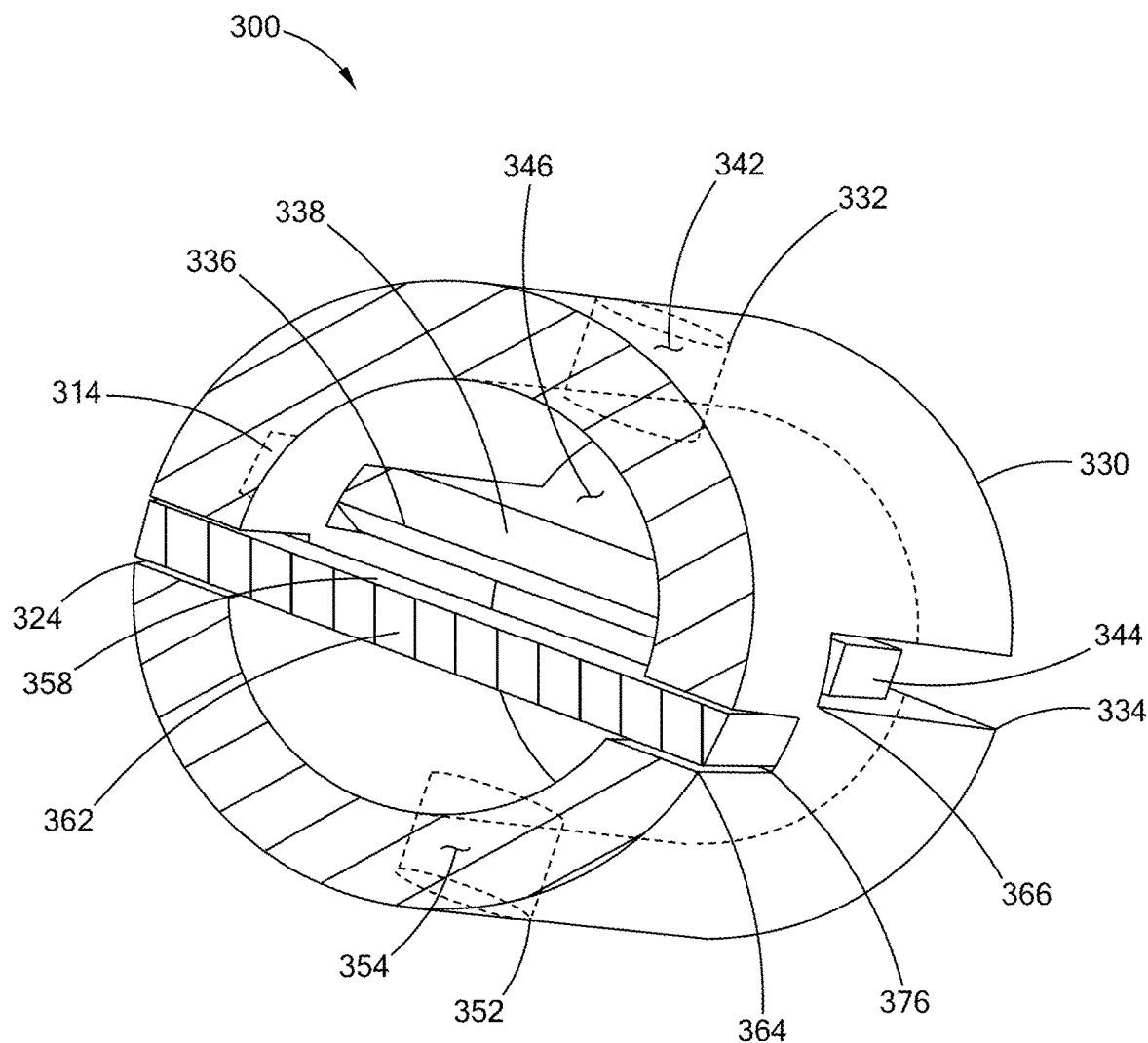
FIG. 3 is a cross-sectional view of the cutting assembly of FIG. 1.

FIG. 3 shows a cross sectional view of the cutting assembly 300. Housing 330 comprises housing lumen 346 running longitudinally therethrough. It further comprises distal cutting element 338 and proximal cutting element 358, positioned parallel to each other and in different cutting planes of the assembly. The cutting elements have their cutting surfaces or blades facing each other. Distal cutting element 338 comprises distal cutting surface 336 and distal shoulder 344. First slot 334 and second slot 314 house distal shoulder 344. In addition, third slot 364 and fourth slot 324 house proximal shoulder 362. As discussed previously, the fit of the shoulders and slots aligns the cutting elements.

The cutting assembly further comprises stop elements 366 and 376 within the slots. First opening 332 with first opening lumen 342 therethrough and second opening 352 with second opening lumen 354 therethrough are configured to house the object, which will run through the cutting assembly perpendicular to the longitudinal axis and the planes of the cutting elements.

Figure 4:
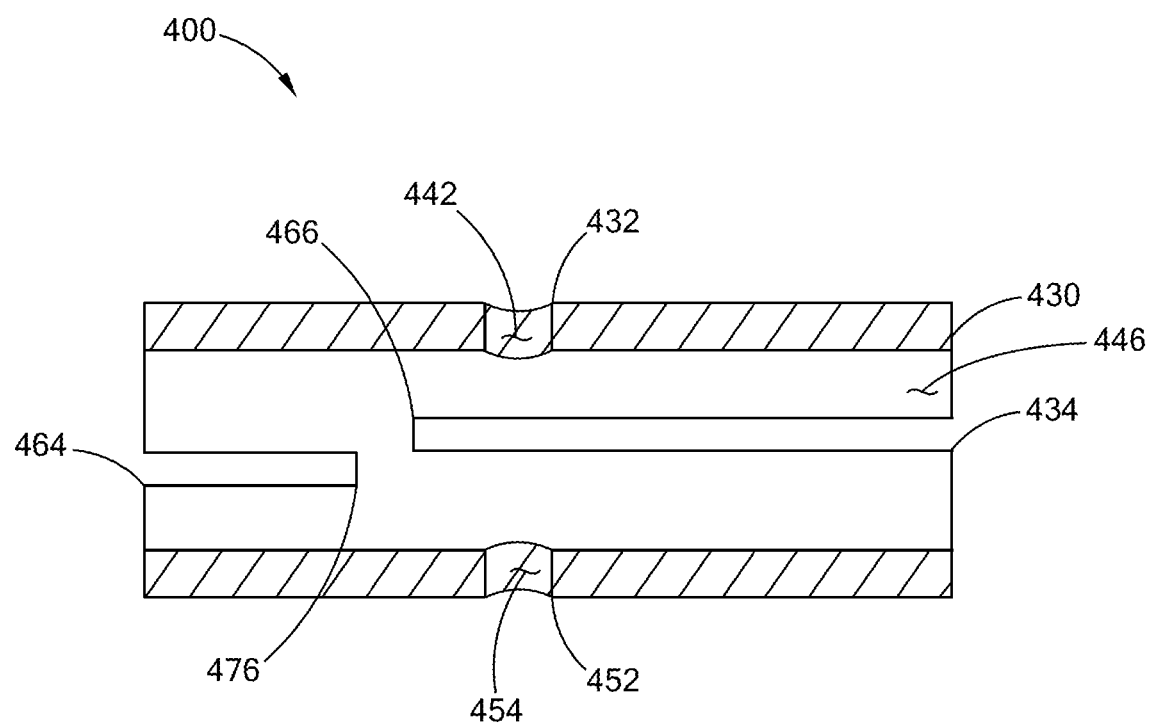
FIG. 4 depicts a partial, side view of a housing of the cutting assembly of FIG. 1.

FIG. 4 shows a side view of one embodiment of the housing 400. This figure omits the cutting elements for simplicity. Housing 430 with housing lumen 446 comprises first slot 434 and third slot 464, having stop elements 466 and 476, respectively. In a preferred embodiment, the proximal and distal shoulders will be restricted by the stop element. However, the proximal and distal cutting surfaces will be allowed to move past the stop element, as it is thinner and smaller than the shoulders (shown in FIG. 2). First opening 432 with first opening lumen 442 and second opening 452 with second opening lumen 454 run perpendicular to the longitudinal axis. The second and fourth slots are not shown here. However, they run parallel to the third and fourth slots, respectively, as shown in FIG. 3.

Figure 5B:
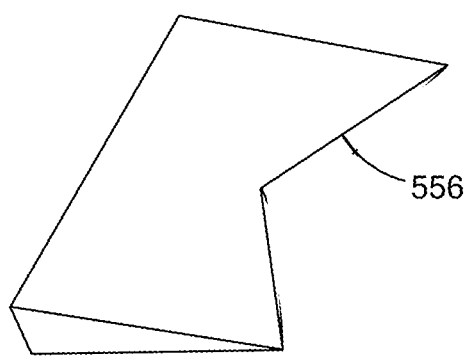

FIG. 5 shows one embodiment 500 of a proximal cutting element. In this embodiment, proximal cutting element 558 comprises first end 560 and second end 556. First end 560 is connected or bonded to the proximal shoulder 562. Proximal shoulder 562 comprises first shoulder end 570 that is configured to be disposed in the third slot, and second shoulder end 572 that is configured to be disposed in the fourth slot. Proximal shoulder 562 further comprises back end 574, which could be connected to the second actuating member (not shown here). FIG. 5B depicts a v-shaped proximal cutting surface 556

Figure 6:
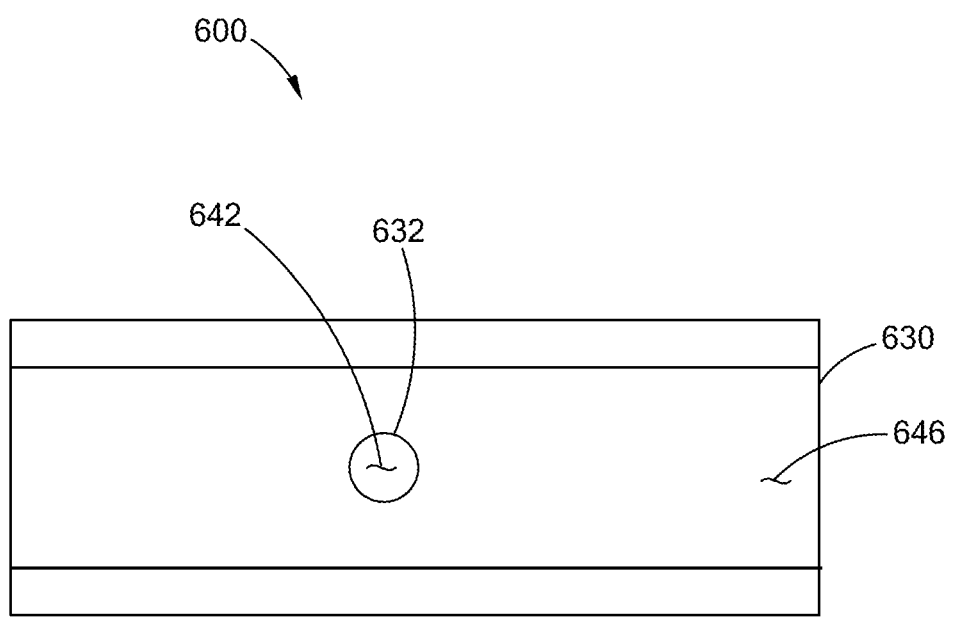
FIG. 6 depicts a partial, top view of the housing of FIG. 4.

FIG. 6 is a top view of one embodiment of the housing. Top view 600 of housing 630 shows housing lumen 646 running along the longitudinal axis. Housing 630 further comprises first opening 632 with first opening lumen 642, running perpendicular to the longitudinal axis. The object positioned through first opening 632 and exits through the second opening on the opposite side of the housing 630. Additionally, the hollow tube could be slidably disposed through the first opening 632 in the first opening lumen 642 to house the object.

Figure 7:
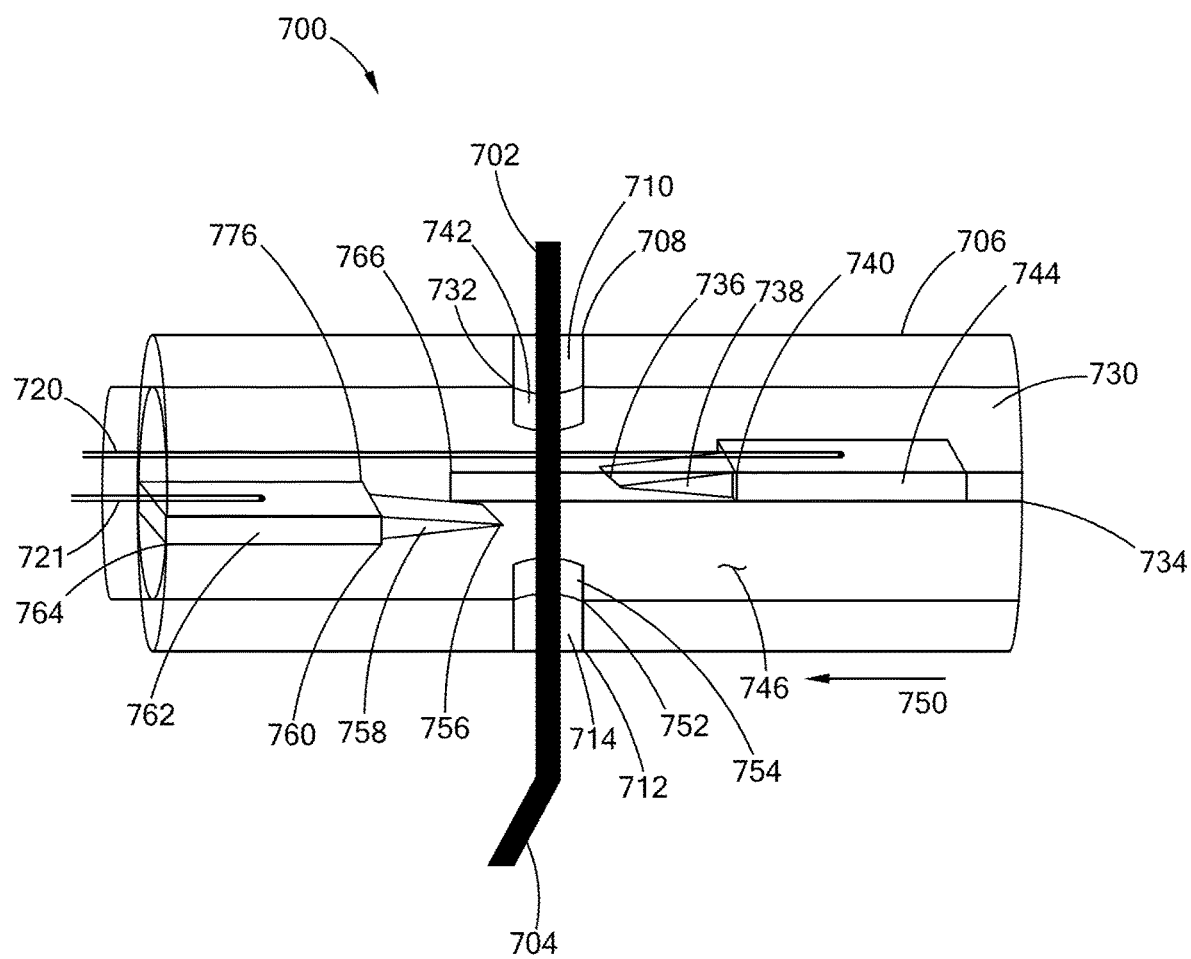
FIG. 7 depicts a partial, side view of the cutting assembly of FIG. 1.

FIG. 7 shows one embodiment of an open position with a suture in the cutting assembly. In cutting assembly 700, suture has an excess portion 702 and a remaining portion 704. The excess portion 702 runs through first opening 732 through first opening lumen 742. Distal cutting element 738, comprising third end 736, fourth end 740, and distal shoulder 744, is in the open position. Distal shoulder 744 fits in first slot 734 and actuates along the longitudinal axis until it contacts stop element 766. Proximal cutting element 758, comprising first end 760, second end 756, and proximal shoulder 762, runs along third slot 764 with stop element 776. The remaining portion 704 travels out second opening 752 through second opening lumen 754. When actuated by the first actuating member 720, the distal cutting element 738 moves or slides along arrow 750 from the open position to the closed position to cut the suture. When cut, the suture will be severed into the excess portion 702 and the remaining portion 704.

In one embodiment, housing 730 is surrounded by or housed within an elongate member 706. Here, the elongate member 706 is disposed outside of housing 730 and makes up the outer bounds of the cutting assembly. In this embodiment, the elongate member 706 also runs along the longitudinal axis, coaxial with the housing 730. The elongate member 706 and housing 730 share housing lumen 746. Further, the elongate member 706 has a third opening 708 with third opening lumen 710 and a fourth opening 712 with fourth opening lumen 714. The third and fourth openings correspond and align with the first and second openings in the housing, (732, 752), respectively. In one embodiment, the elongate member 706 is a catheter and housing 730 is a cannula. Elongate member 706 aids in the flexibility of delivering the cutting assembly to the ideal position within the body while still maintaining the stiffness necessary in housing 730 to keep the blades or cutting elements in their position.

Figure 8:
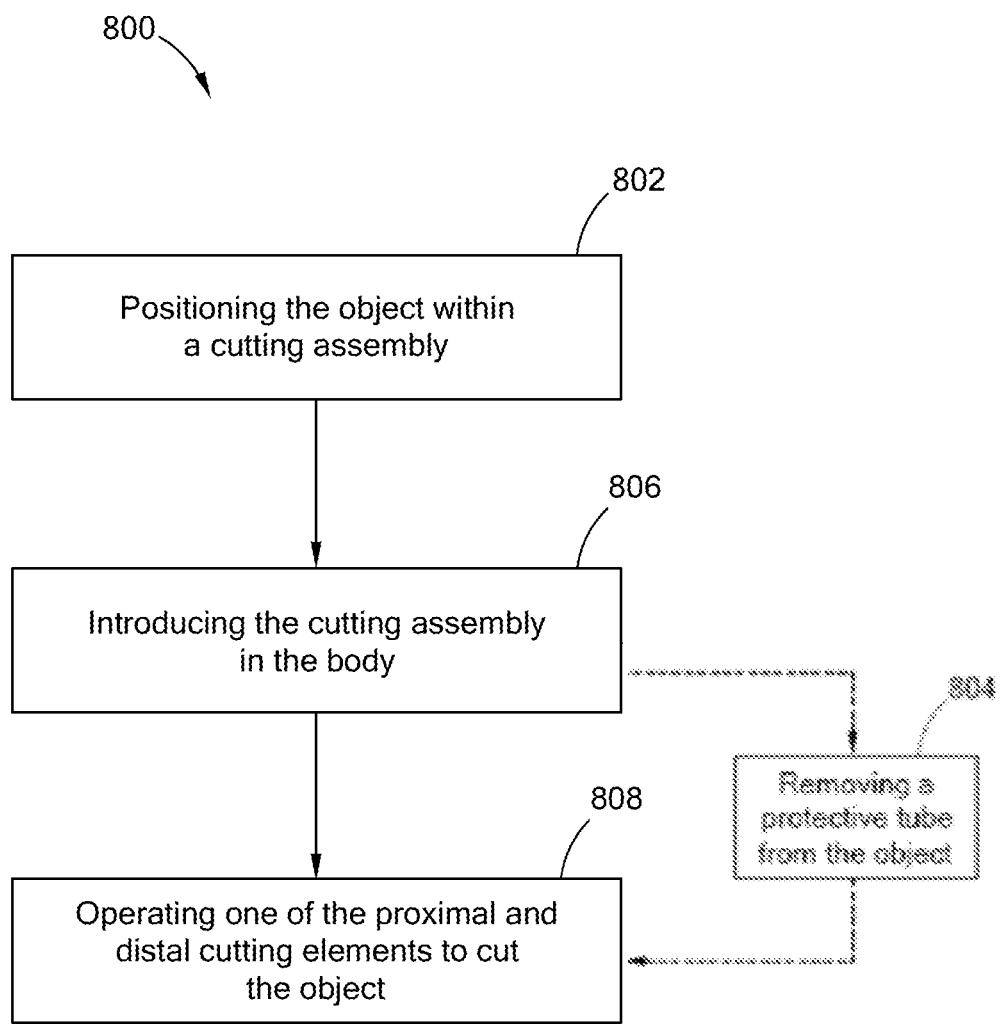
FIG. 8 is a flow diagram of a method of use of a cutting assembly in accordance with one embodiment of the present invention.

FIG. 8 shows a method 800 of using the cutting assembly. In step 802, the practitioner orients or positions the object in the cutting assembly at a position for cutting. He or she positions the object by loading or feeding it through the first and second openings. In one embodiment, the object will be loaded outside of the body. It may be loaded by pushing the excess portion through the openings, like threading a needle. In an alternative embodiment, the excess portion may be threaded through the openings using a thin ridged guide, such as a metal guide, to grab the suture and pull it back through the openings.

In step 806, the practitioner introduces the cutting assembly along the object to the position for cutting in the body. The practitioner will take into consideration surrounding body structures to determine the position for cutting. This can be achieved even when visualization of the cutting site is poor or far remote from the proximal end or handle. Optionally, the object may be disposed in a tube. In step 804, the practitioner may remove the tube from the object prior to cutting.

In step 808, the practitioner operates the one of the proximal and distal cutting elements to cut the object. At this point, the remaining portion is cleanly cut at the incision site.

FIGS. 9A-B depict a side view of the cutting assembly 100 attached to a shaft 906. When the physician is ready to use the cutting assembly 100, he or she may use a hub or handle 908 located at a proximal end 911 of the shaft 906 to manipulate the cutting assembly 100 to the desired cutting location. The shaft 906 extends from the proximal portion 911 to a distal portion 912 adjacent to the cutting assembly 100. The cutting assembly 100 may be integrally formed with the shaft 906 such that the handle 908 and the shaft 906 may manipulate the cutting assembly 100 to make the desired cut.

One skilled in this art will understand that the handle could further incorporate known mechanisms to actuate the cutting surfaces with the actuators (as discussed above). FIG. 9B depicts the handle 908 as a three ring handle, which may assist in manipulation. Further, the shaft 906 may be withdrawn from the body after cutting. It should be understood that above disclosure of the cutting assembly and method of cutting is merely exemplary of this system, and not intended to limit the scope of the disclosure. Other parts, assemblies, and methods may be used without falling beyond the scope and spirit of the present disclosure, as defined in the following claims.

The invention claimed is:

1. A cutting assembly for cutting an object in a body of a patient, the cutting assembly comprising:
   a housing being tubular and having a proximal end and extending along a longitudinal axis to a distal end with a housing lumen formed therethrough;
   a proximal cutting element disposed in the housing lumen and comprising a first end distal the proximal end, the first end extending along the longitudinal axis to a second end, defining a first plane, the second end comprising a proximal cutting surface; and
   a distal cutting element disposed in the housing lumen distal the proximal cutting element and comprising a third end extending along the longitudinal axis to a fourth end, defining a second plane being parallel with the first plane, the third end comprising a distal cutting surface, one of the proximal and distal cutting elements being operable along the longitudinal axis such that the cutting assembly has an open position and a closed position, the distal cutting surface being distal the proximal cutting surface a first distance (d) in the open position, the distal cutting surface being proximal the proximal cutting surface a second distance (o) in the closed position, the housing having a first opening formed therethrough between the proximal and distal ends, and a second opening formed therethrough and located across the housing lumen from the first opening, such that the object is disposed in the first and second openings and between the proximal and distal cutting surfaces, the proximal and distal cutting surfaces cooperating to cut the object in the body.

2. The cutting assembly of claim 1 wherein the housing comprises an inner wall forming a first slot and a second slot being parallel with the first slot, the first slot being formed across the housing lumen from the second slot, the first and second slots being parallel with the longitudinal axis.

3. The cutting assembly of claim 2 wherein the inner wall forms a third slot proximal the first slot and a fourth slot proximal the second slot, the third slot being parallel with and formed across the housing lumen from the fourth slot, the third and fourth slots being parallel with the longitudinal axis.

4. The cutting assembly of claim 3 wherein the proximal cutting element comprises a proximal shoulder disposed on the first end, the proximal shoulder being slidably received in the third and fourth slots.

5. The cutting assembly of claim 4 wherein the distal cutting element comprises a distal shoulder disposed on the fourth end, the distal shoulder being slidably received in the first and second slots.

6. The cutting assembly of claim 5 wherein one of the first, second, third, and fourth slots comprises a stop element, the stop element disposed in the one of the first, second, third, and fourth slots to stop one of the proximal and distal shoulders from sliding.

7. The cutting assembly of claim 1, further comprising a hollow tube disposed in the first and second openings, the object being disposed in the hollow tube.

8. The cutting assembly of claim 7 wherein the hollow tube is slidably received in the first and second openings.

9. The cutting assembly of claim 1 wherein the cutting assembly further comprises an elongate member disposed about the housing.

10. The cutting assembly of claim 1 wherein the first distance (d) being sized and shaped to accommodate the object being a suture.

11. The cutting assembly of claim 1 further comprising an actuating member operating the one of the proximal and distal cutting elements.

12. The cutting assembly of claim 11 wherein the actuating member is a first actuating member being mechanically connected to and slidably operating the distal cutting element, the proximal cutting element being stationary.

13. The cutting assembly of claim 11 wherein the actuating member is a first actuating member slidably operating the distal cutting element and a second actuating member slidably operating the proximal cutting element such that the first and second actuating members slide the distal and proximal cutting elements, respectively, between the open and closed positions of the cutting assembly.

14. The cutting assembly of claim 11 further comprises a handle proximal the proximal end, the actuating member being connected to the handle and distally extending along the longitudinal axis to the one of the proximal and distal cutting elements.

15. The cutting assembly of claim 1 wherein the proximal and distal cutting surfaces are V-shaped.

16. A cutting assembly for cutting an object in a body of a patient, the cutting assembly comprising:
  a housing being tubular and having a proximal end and extending along a longitudinal axis to a distal end with a housing lumen formed therethrough;
  a proximal cutting element disposed in the housing lumen and comprising a first end distal the proximal end, the first end extending along the longitudinal axis to a second end, defining a first plane, the second end comprising a proximal cutting surface;
  a distal cutting element disposed in the housing lumen distal the proximal cutting element and comprising a third end extending along the longitudinal axis to a fourth end, defining a second plane being parallel with the first plane, the third end comprising a distal cutting surface, the distal cutting element being operable along the longitudinal axis such that the cutting assembly has an open position and a closed position;
  an actuating member for operating the one of the proximal and distal cutting elements, the actuating member being a first actuating member mechanically connected to and slidably operating the distal cutting element, the proximal cutting element being stationary, the first actuating member comprising a return member being a spring, the actuating member moves the cutting assembly from the open position to the closed position, the spring biasingly moves the cutting assembly from the closed position to the open position;
  the distal cutting surface being distal the proximal cutting surface a first distance (d) in the open position, the distal cutting surface being proximal the proximal cutting surface a second distance (o) in the closed position, the proximal and distal cutting surfaces cooperating to cut the object in the body.

17. A cutting assembly for cutting an object in a body of a patient, the cutting assembly comprising:
  a housing being tubular and having a proximal end and extending along a longitudinal axis to a distal end with a housing lumen formed therethrough;
  a proximal cutting element disposed in the housing lumen and comprising a first end distal the proximal end, the first end extending along the longitudinal axis to a second end, defining a first plane, the second end comprising a proximal cutting surface;
  a distal cutting element disposed in the housing lumen distal the proximal cutting element and comprising a third end extending along the longitudinal axis to a fourth end, defining a second plane being parallel with the first plane, the third end comprising a distal cutting surface, at least one of the proximal and distal cutting elements being operable along the longitudinal axis such that the cutting assembly has an open position and a closed position; and
  an actuating member for operating the one of the proximal and distal cutting elements, the actuating member comprising a first actuating member comprising a first metal stylet slidably operating the distal cutting element, and a second actuating member comprising a second metal stylet slidably operating the proximal cutting element, such that the first and second actuating members slide the distal and proximal cutting elements, respectively, between the open and closed positions of the cutting assembly,
  the distal cutting surface being distal the proximal cutting surface a first distance (d) in the open position, the distal cutting surface being proximal the proximal cutting surface a second distance (o) in the closed position, the proximal and distal cutting surfaces cooperating to cut the object in the body.

18. A method of cutting an object in a body of a patient, the method comprising:

positioning the object within a cutting assembly, the cutting assembly comprising:
- a housing being tubular and having a proximal end and extending along a longitudinal axis to a distal end with a housing lumen formed therethrough;
- a proximal cutting element disposed in the housing lumen and comprising a first end distal the proximal end, the first end extending along the longitudinal axis to a second end, defining a first plane, the second end comprising a proximal cutting surface; and
- a distal cutting element disposed in the housing lumen distal the proximal cutting element and comprising a third end extending along the longitudinal axis to a fourth end, defining a second plane being parallel the first plane, the third end comprising a distal cutting surface, one of the proximal and distal cutting elements being operable along the longitudinal axis such that the cutting assembly has an open position and a closed position, the distal cutting surface being distal the proximal cutting surface a first distance (d) in the open position, the distal cutting surface being proximal the proximal cutting surface a second distance (o) in the closed position, the proximal and distal cutting surfaces cooperating to cut the object in the body;

introducing the cutting assembly in the body; and operating the one of the proximal and distal cutting elements to cut the object.

19. The method of claim 18 wherein the step of positioning the object comprises positioning the obect being a suture.

\* \* \* \* \*